(12) United States Patent
Buettelmann et al.

(10) Patent No.: US 7,388,025 B2
(45) Date of Patent: Jun. 17, 2008

(54) 3-ARYL-ISOXAZOLE-4-CARBONYL-BENZOFURAN DERIVATIVES

(75) Inventors: Bernd Buettelmann, Schopfheim (DE); Bo Han, Shanghai (CN); Henner Knust, Rheinfelden (DE); Matthias Nettekoven, Grenzach-Wyhlen (DE); Andrew Thomas, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 37 days.

(21) Appl. No.: 11/590,571

(22) Filed: Oct. 31, 2006

(65) Prior Publication Data

US 2007/0105922 A1    May 10, 2007

(30) Foreign Application Priority Data

Nov. 9, 2005    (EP) .................. 05110503

(51) Int. Cl.
*A61K 31/42* (2006.01)
*C07D 413/02* (2006.01)

(52) U.S. Cl. ...................... 514/378; 548/248
(58) Field of Classification Search ........... 514/378; 548/248
See application file for complete search history.

(56) References Cited

U.S. PATENT DOCUMENTS

2004/0006226 A1    1/2004  Ladduwahetty et al.

FOREIGN PATENT DOCUMENTS

WO    WO 01/029015    4/2001
WO    WO 03/004027    1/2003

OTHER PUBLICATIONS

McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Burke, et al., Journal of Natural Products, 1986, vol. 49, pp. 522-523.
Hamper, et al., J. Agric. Food Chem. (1995), vol. 43, pp. 219-228.

*Primary Examiner*—Kamal A Saeed
(74) *Attorney, Agent, or Firm*—George W. Johnston; Patricia S. Rocha-Tramaloni; Kimberly J. Prior

(57) ABSTRACT

The present invention is concerned with 3-aryl-isoxazole-4-carbonyl-benzofuran derivatives of formula I

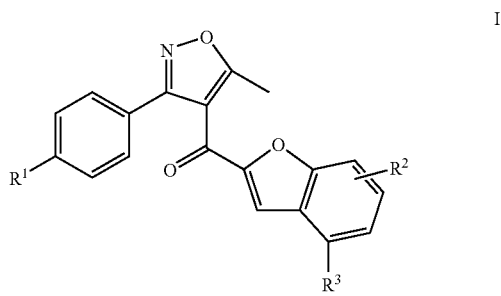

wherein
$R^1$, $R^2$, and $R^3$ are as defined in the specification and claims and with their pharmaceutically acceptable acid addition salts. These compounds have a high affinity and selectivity for GABA A α5 receptor binding sites and might be useful as cognitive enhancer or for the treatment of cognitive disorders like Alzheimer's disease.

27 Claims, No Drawings

3-ARYL-ISOXAZOLE-4-CARBONYL-BENZOFURAN DERIVATIVES

PRIORITY TO RELATED APPLICATIONS

This application claims the benefit of European Application No. 05110503.9, Filed Nov. 9, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides 3-aryl-isoxazole-4-carbonyl-benzofuran derivatives of formula I

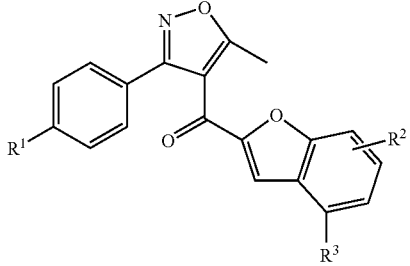

wherein
 $R^1$ is hydrogen or halogen;
 $R^2$ is hydrogen, halogen, hydroxy, lower alkoxy, $OCF_3$, or —$OCH_2$—R,
 $R^3$ is hydrogen or lower alkoxy; or
 $R^2$ and $R^3$ together are —CH=CH—CH=CH—;
 R is aryl or heteroaryl, each of which is optionally substituted by halogen or lower alkyl, or is C(O)NH-lower alkyl or —C(O)-heteroaryl, wherein the heteroaryl group is optionally substituted by lower alkyl or phenyl, and pharmaceutically acceptable acid addition salts thereof.

The invention also provides pharmaceutical compositions comprising a therapeutically effective amount of a compound of formula I and a pharmaceutically acceptable carrier. The invention further provides methods for preparing the compounds and compositions of the invention.

This class of compounds has high affinity and selectivity for GABA A α5 receptor binding sites and might be useful as a cognitive enhancer or for the treatment of cognitive disorders like Alzheimer's disease.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain alkyl group containing from 1-7, preferably from 1-4 carbon atoms, for example, methyl, ethyl, propyl, isopropyl, n-butyl, i-butyl, t-butyl and the like.

The term "lower alkoxy" denotes a lower alkyl residue in as defined above bound via an oxygen atom. Examples of "lower alkoxy" residues include methoxy, ethoxy, isopropoxy and the like.

The term "aryl" denotes an unsaturated carbon ring, for example a phenyl, benzyl or naphthyl group. A preferred aryl group is phenyl.

The term "halogen" denotes chlorine, iodine, fluorine and bromine.

The term "cycloalkyl" denotes a cyclic alkyl ring, having from 3 to 7 carbon ring atoms, for example, cyclopropyl, cyclopentyl or cyclohexyl.

The term "heteroaryl" denotes an aromatic 5 or 6 membered ring containing from one to three heteroatoms, selected from N, O and S atoms. Examples of such aromatic heteroaryl groups include pyridinyl, triazolyl, isoxazolyl, furanyl, thiophenyl, imidazolyl, oxazolyl and pyrazinyl.

The aryl, 5- or 6-membered heteroaryl, heterocycloalkyl, and cycloalkyl groups are unsubstituted or substituted by one or more substituents. Examples of such substituents include halogen, lower alkyl, and $SO_2$-lower alkyl, as well as those groups depicted in the specific examples appended hereto.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides 3-aryl-isoxazole-4-carbonyl-benzofuran derivatives of formula I

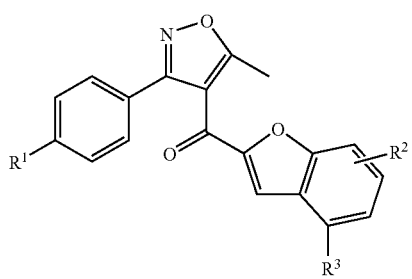

wherein $R^1$ is hydrogen or halogen;

$R^2$ is hydrogen, halogen, hydroxy, lower alkoxy, $OCF_3$, or —$OCH_2$—R, $R^3$ is hydrogen or lower alkoxy; or $R^2$ and $R^3$ together are —CH=CH—CH=CH—;

R is aryl or heteroaryl, each of which is optionally substituted by halogen or lower alkyl, or is C(O)NH-lower alkyl or —C(O)-heteroaryl, wherein the heteroaryl group is optionally substituted by lower alkyl or phenyl, and pharmaceutically acceptable acid addition salts thereof.

Preferred are compounds, which have a binding activity (hKi) of lower than 100 nM and are selective for GABA A α5 subunits and are relatively free of activity at GABA A α1, α2 and α3 receptor binding sites. Most preferred are compounds which have a binding activity (hKi) of lower than 35 nM.

Preferred compounds of formula I are those, in which $R^1$ is hydrogen. Especially preferred compounds from this group are those, wherein $R^3$ is hydrogen, in particular those in which $R^2$ is halogen, hydroxy, $OCF_3$ or lower alkoxy, for example the following compounds (7-bromo-benzofuran-2-yl)-(5-methyl-3-phenyl-isoxazol-4-yl)-methanone, (7-hydroxy-2-benzofuranyl)(5-methyl-3-phenyl-4-isoxazolyl)methanone, (7-methoxy-benzofuran-2-yl)-(5-methyl-3-phenyl-isoxazol-4-yl)-methanone, (7-ethoxy-benzofuran-2-yl)-(5-methyl-3-phenyl-isoxazol-4-yl)-methanone, (6-hydroxy-benzofuran-2-yl)-(5-methyl-3-phenyl-isoxazol-4-yl)-methanone, (6-methoxy-benzofuran-2-yl)-(5-methyl-3-phenyl-isoxazol-4-yl)-methanone, (5-methoxy-benzofuran-2-yl)-(5-methyl-3-phenyl-isoxazol-4-yl)-methanone, (5-methoxy-benzofuran-2-yl)-(5-methyl-3-phenyl-isoxazol-4-yl)-methanone and (5-methyl-3-phenyl-isoxazol-4-yl)-(5-trifluoromethoxy-benzofuran-2-yl)-methanone.

Preferred compounds of formula I are further those, in which $R^1$ and $R^3$ are hydrogen and $R^2$ is —$OCH_2$—C(O)NH-lower alkyl or —$OCH_2$-heteroaryl, optionally substituted by halogen or lower alkyl, for example the following compounds N-isopropyl-2-[2-(5-methyl-3-phenyl-isoxazole-4-carbonyl)-benzofuran-7-yloxy]-acetamide, (5-methyl-3-phenyl-isoxazol-4-yl)-[7-(pyridin-2-yl-methoxy)-benzofuran-2-yl]-methanone, (5-methyl-3-phenyl-isoxazol-4-yl)-[7-(pyridin-3-yl-methoxy)-benzofuran-2-yl]-methanone, (5-methyl-3-phenyl-isoxazol-4-yl)-[7-(pyridin-4-yl-methoxy)-benzofuran-2-yl]-methanone and

[7-(3-methyl-isoxazol-5-ylmethoxy)-benzofuran-2-yl]-(5-methyl-3-phenyl-isoxazol-4-yl)-methanone.

Preferred compounds of formula I are further those, in which $R^1$ is hydrogen, $R^3$ is lower alkoxy and $R^2$ is lower alkoxy, for example the following compound (4,6-dimethoxy-benzofuran-2-yl)-(5-methyl-3-phenyl-isoxazol-4-yl)-methanone.

Preferred compounds of formula I are those, in which $R^1$ is halogen. Especially preferred are compounds, wherein $R^3$ is hydrogen and $R^2$ is hydrogen, hydroxy, lower alkoxy or —$OCH_2$C(O)NH-lower alkyl, for example the following compounds benzofuran-2-yl-[3-(4-bromo-phenyl)-5-methyl-isoxazol-4-yl]-methanone,

[3-(4-bromo-phenyl)-5-methyl-isoxazol-4-yl]-(7-methoxy-benzofuran-2-yl)-methanone,

[3-(4-bromo-phenyl)-5-methyl-isoxazol-4-yl]-(7-ethoxy-benzofuran-2-yl)-methanone, 2-{2-[3-(4-bromo-phenyl)-5-methyl-isoxazole-4-carbonyl]-benzofuran-7-yloxy}-N-isopropyl-acetamide,

[3-(4-bromo-phenyl)-5-methyl-isoxazol-4-yl]-(6-hydroxy-benzofuran-2-yl)-methanone,

[3-(4-bromo-phenyl)-5-methyl-isoxazol-4-yl]-(6-methoxy-benzofuran-2-yl)-methanone,

[3-(4-bromo-phenyl)-5-methyl-isoxazol-4-yl]-(5-hydroxy-benzofuran-2-yl)-methanone and

[3-(4-bromo-phenyl)-5-methyl-isoxazol-4-yl]-(5-methoxy-benzofuran-2-yl)-methanone.

Preferred compounds of formula I are further those, in which $R^2$ is halogen, $R^3$ is lower alkoxy and $R^2$ is hydrogen, for example the following compound [3-(4-bromo-phenyl)-5-methyl-isoxazol-4-yl]-(4-methoxy-benzofuran-2-yl)-methanone.

Other preferred compounds are those wherein $R^3$ is hydrogen. Alternatively, preferred compounds are those in which $R^3$ is lower alkoxy.

Preferred compounds of the invention also are those in which $R^2$ is $OCH_2R$. Especially preferred compounds from this group are those, wherein R is an aryl group, such as an unsubstituted or substituted phenyl group. Other preferred compounds from this group are those, wherein R is a heteroaryl group, such as pyridinyl, oxazolyl, or triazolyl. Additional preferred compounds within this group are those in which R is C(O)NH-lower alkyl.

Preferred compounds of the invention are those wherein $R^2$ is hydrogen, halogen, hydroxy, $OCH_3$ or $OCF_3$. Other preferred compounds are those in which $R^2$ and $R^3$ together are —CH═CH—CH═CH—.

The present compounds of formula I and their pharmaceutically acceptable salts can be prepared by methods known in the art, for example, by processes described below, which process comprises reacting a compound of formula

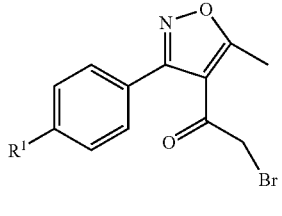

II with a compound of formula

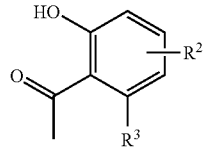

III in the presence of potassium carbonate to give a compound of formula

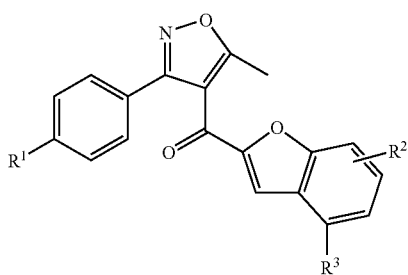

I wherein $R^1$, $R^2$ and $R^3$ are as described above, and, if desired, converting a compound of formula I into a pharmaceutically acceptable salt.

The starting materials of formulas II and III are known compounds or can be prepared according to methods known in the art.

According to reaction step above, compounds of formula I can be prepared as follows: To a solution of the bromo ketone II (commercially available for $R^1$═H) in DMF at room temperature was added the appropriately substituted salicylaldehyde of formula III and the mixture stirred vigorously for about 2 h. Where $R^2$═OH the products can then be further transformed as shown in Scheme 1.

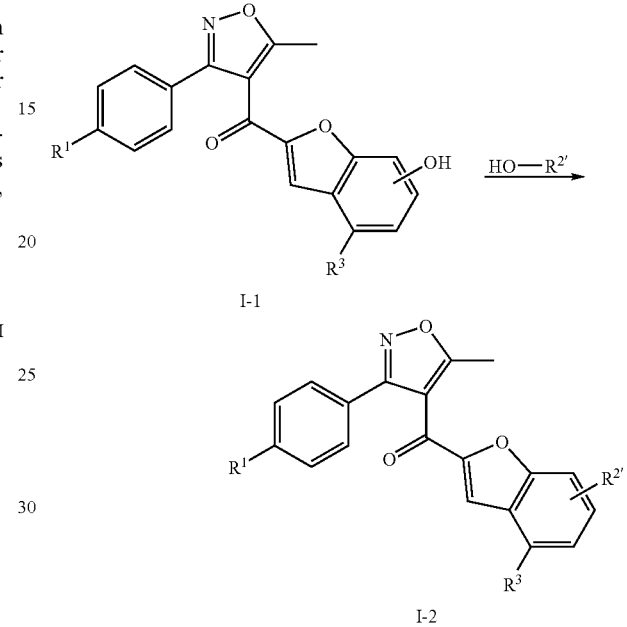

Scheme 1 wherein $R^{2'}$ is lower alkyl, $CF_3$, —$CH_2$—R for R being aryl or heteroaryl, optionally substituted by halogen or lower alkyl, or being C(O)NH-lower alkyl, or —C(O)-heteroaryl, wherein the heteroaryl group is optionally substituted by lower alkyl or phenyl.

To a solution of a compound of formula I-1 in THF and the appropriate alcohol of formula HO—$R^{2'}$, triphenylphosphine is added and the resulting mixture is cooled to 0° C. Then diethyl azodicarboxylate is added and the reaction mixture allowed to warm up to room temperature overnight. Alternatively, the compound of formula I-1 is dissolved in THF or DMF and potassium carbonate added followed by addition of the appropriate halide at room temperature and the resulting mixture is stirred overnight.

As mentioned earlier, the compounds of formula I and their pharmaceutically usable salts possess valuable pharmacological properties. It has been found that the compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell memebrans, [3H]flumazenil at a concentration of 1 nM for $\alpha 1$, $\alpha 2$, $\alpha 3$ subunits and 0.5 nM for $\alpha 5$ subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from a5 subunits of the rat GABA A receptor of 100 nM or less. In a preferred embodiment the compounds of the invention are binding selective for the $\alpha 5$ subunit relative to the $\alpha 1$, $\alpha 2$ and $\alpha 3$ subunit.

| Example No. | Ki[nM] h$\alpha$5 |
| --- | --- |
| 1 | 15.2 |
| 2 | 17.8 |
| 3 | 7.5 |
| 4 | 6.9 |
| 5 | 4.0 |
| 6 | 6.5 |
| 8 | 16.7 |
| 9 | 31.3 |
| 10 | 27.9 |
| 13 | 1.8 |
| 14 | 13.8 |
| 15 | 18.9 |
| 16 | 3.7 |
| 17 | 3.5 |
| 19 | 20.0 |
| 20 | 41.6 |
| 21 | 1.4 |
| 22 | 4.6 |
| 23 | 10.1 |
| 25 | 10.6 |
| 26 | 4.3 |
| 27 | 13.7 |
| 28 | 8.1 |
| 29 | 11.7 |
| 30 | 17.4 |
| 31 | 3.7 |
| 32 | 9.4 |
| 33 | 32.9 |
| 34 | 36.3 |
| 35 | 36.4 |
| 36 | 35.9 |
| 37 | 2.3 |
| 38 | 15.1 |
| 39 | 63.8 |
| 40 | 9.3 |
| 41 | 3.1 |
| 42 | 4.6 |
| 43 | 2.9 |
| 44 | 4.8 |

The present invention also provides pharmaceutical compositions containing compounds of formula I and/or their pharmaceutically usable acid addition salts. Such compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injection solutions.

Compounds of the invention have a high affinity and selectivity for GABA A $\alpha 5$ receptor binding sites. The compounds can be used as a cognitive enhancer or for the treatment of cognitive disorders like Alzheimer's disease. Therefore, the invention provides a method for treating Alzheimer's disease which comprises administering to an individual, a therapeutically effective amount of a compound of formula I or a pharmaceutically acceptable acid addition salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|                           | mg/tablet |
|---------------------------|-----------|
| Active substance          | 5         |
| Lactose                   | 45        |
| Corn starch               | 15        |
| Microcrystalline cellulose| 34        |
| Magnesium stearate        | 1         |
| Tablet weight             | 100       |

EXAMPLE B

Capsules of the following composition are manufactured:

|                    | mg/capsule |
|--------------------|------------|
| Active substance   | 10         |
| Lactose            | 155        |
| Corn starch        | 30         |
| Talc               | 5          |
| Capsule fill weight| 200        |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|                  | mg/supp. |
|------------------|----------|
| Active substance | 15       |
| Suppository mass | 1285     |
| Total            | 1300     |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-44 are provided for illustration of the invention. They should not be considered as limiting the scope of the invention, but merely as being representative thereof.

EXAMPLE 1

Benzofuran-2-yl-(5-methyl-3-phenyl-isoxazol-4-yl)-methanone

To a solution of 4-(bromoacetyl)-5-methyl-3-phenylisoxazole (commercially available) (140 mg, 0.5 mmol) in DMF (0.5 mL) was added salicylaldehyde (61 mg, 53 μL, 0.5 mmol) followed by potassium carbonate (138 mg, 1.0 mmol) and the resulting mixture stirred vigorously at room temperature for 2 h. The mixture was then poured onto ice-water, and extracted with ethyl acetate. The combined organic layers were then washed with water and brine, dried over $Na_2SO_4$ and evaporated. Purification by chromatography ($SiO_2$, heptane:ethyl acetate:=100:0 to 1:1) afforded the title compound (131 mg, 86%) as a white solid. MS m/e: 304.0 $[M+H]^+$.

EXAMPLE 2

(7-Fluoro-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 3-fluoro-2-hydroxybenzaldehyde instead of salicylaldehyde) which was obtained as a white solid (125 mg, 78%). MS m/e: 322.4 $[M+H]^+$.

EXAMPLE 3

(7-Bromo-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 3-bromo-2-hydroxybenzaldehyde instead of salicylaldehyde) which was obtained as a white solid (1.4 g, 51%). MS m/e: 382.0/384.1 $[M+H]^+$.

EXAMPLE 4

(7-Hydroxy-2-benzofuranyl)(5-methyl-3-phenyl-4-isoxazolyl)methanone

As described for example 1, 4-(bromoacetyl)-5-methyl-3-phenylisoxazole (commercially available) (2.5 g, 359 mmol) was converted to the title compound (using 2,3-dihydroxybenzaldehyde instead of salicylaldehyde) which was obtained as a white solid (3.2 g, 55%). MS m/e: 318.0 $[M-H]^-$. *Journal of Natural Products,* 1986, 49, 522-552.

EXAMPLE 5

(7-Methoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using o-vanillin instead of salicylaldehyde) which was obtained as a white solid (90 mg, 54%). MS m/e: 334.4 $[M+H]^+$.

EXAMPLE 6

(7-Ethoxy-benzofuran-2-yl)-(5-methyl-3-phenyl-isoxazol-4-yl)-methanone

To a solution of (7-hydroxy-2-benzofuranyl)(5-methyl-3-phenyl-4-isoxazolyl)methanone (example 4) (100 mg, 0.31 mmol) in THF (3.1 mL) was added ethanol (19 mg, 24 μL, 0.42 mmol) and triphenylphosphine (109 mg, 0.42 mmoL) at room temperature. The resulting mixture was then cooled to 0° C. and diethyl azodicarboxylate (73 mg, 65 μL, 0.42 mmol) added. The resulting mixture was maintained at 0° C.

for 30 min and then allowed to warm up to room temperature overnight. The mixture was then adsorbed onto SiO$_2$ and purification by chromatography (SiO$_2$, heptane:ethyl acetate:=100:0 to 75:25) afforded the title compound (90 mg, 83%) as a white solid. MS m/e: 348.4 [M+H]$^+$.

EXAMPLE 7

(7-Benzyloxy-benzofuran-2-yl)-(5-methyl-3-phenyl-isoxazol-4-yl)-methanone

As described for example 6, (7-hydroxy-2-benzofuranyl)(5-methyl-3-phenyl-4-isoxazolyl)methanone (example 4) (100 mg, 0.31 mmol) was converted to the title compound (using benzyl alcohol instead of ethanol) which was obtained as a white solid (108 mg, 84%). MS m/e: 410.3 [M+H]$^+$.

EXAMPLE 8

(5-Methyl-3-phenyl-isoxazol-4-yl)-[7-(pyridin-2-ylmethoxy)-benzofuran-2-yl]-methanone As described for example 6, (7-hydroxy-2-benzofuranyl)(5-methyl-3-phenyl-4-isoxazolyl)methanone (example 4) (100 mg, 0.31 mmol) was converted to the title compound [using 2-(hydroxymethyl)pyridine instead of ethanol] which was obtained as a white solid (85 mg, 66%). MS m/e: 411.0 [M+H]$^+$.

EXAMPLE 9

(5-Methyl-3-phenyl-isoxazol-4-yl)-[7-(pyridin-3-ylmethoxy)-benzofuran-2-yl]-methanone As described for example 6, (7-hydroxy-2-benzofuranyl)(5-methyl-3-phenyl-4-isoxazolyl)methanone (example 4) (100 mg, 0.31 mmol) was converted to the title compound [using 3-(hydroxymethyl)pyridine instead of ethanol] which was obtained as a white solid (77 mg, 60%). MS m/e: 411.0 [M+H]$^+$.

EXAMPLE 10

(5-Methyl-3-phenyl-isoxazol-4-yl)-[7-(pyridin-4-ylmethoxy)-benzofuran-2-yl]-methanone As described for example 6, (7-hydroxy-2-benzofuranyl)(5-methyl-3-phenyl-4-isoxazolyl)methanone (example 4) (100 mg, 0.31 mmol) was converted to the title compound [using 4-(hydroxymethyl)pyridine instead of ethanol] which was obtained as a white solid (54 mg, 42%). MS m/e: 411.0 [M+H]$^+$.

EXAMPLE 11

[7-(3-Fluoro-benzyloxy)-benzofuran-2-yl]-(5-methyl-3-phenyl-isoxazol-4-yl)-methanone As described for example 6, (7-hydroxy-2-benzofuranyl)(5-methyl-3-phenyl-4-isoxazolyl)methanone (example 4) (100 mg, 0.31 mmol) was converted to the title compound (using 3-fluorobenzyl alcohol instead of ethanol) which was obtained as a white solid (94 mg, 70%). MS m/e: 428.3 [M+H]$^+$.

EXAMPLE 12

[7-(4-Fluoro-benzyloxy)-benzofuran-2-yl]-(5-methyl-3-phenyl-isoxazol-4-yl)-methanone As described for example 6, (7-hydroxy-2-benzofuranyl)(5-methyl-3-phenyl-4-isoxazolyl)methanone (example 4) (100 mg, 0.31 mmol) was converted to the title compound (using 4-fluorobenzyl alcohol instead of ethanol) which was obtained as a white solid (77 mg, 57%). MS m/e: 428.3 [M+H]$^+$.

EXAMPLE 13

N-Isopropyl-2-[2-(5-methyl-3-phenyl-isoxazole-4-carbonyl)-benzofuran-7-yloxy]-acetamide To a solution of (7-hydroxy-2-benzofuranyl)(5-methyl-3-phenyl-4-isoxazolyl)methanone (example 4) (100 mg, 0.31 mmol) in DMF (5 mL) was added N-(chloroacetyl)isopropylamine (47 mg, 0.34 mmol) and potassium carbonate (173 mg, 1.25 mmol) and the reaction mixture was stirred at room temperature for 4 h. The mixture was then poured onto ice-water, and extracted with ethyl acetate. The combined organic layers were then washed with water and brine, dried over Na$_2$SO$_4$ and evaporated. Purification by chromatography (SiO$_2$, heptane:ethyl acetate:=100:0 to 1:1) afforded the title compound (37 mg, 28%) as a white solid. MS m/e: 419.3 [M+H]$^+$.

EXAMPLE 14

(5-Methyl-3-phenyl-isoxazol-4-yl)-[7-(2-methyl-2H-[1,2,4]triazol-3-ylmethoxy)-benzofuran-2-yl]-methanone As described for example 13, (7-hydroxy-2-benzofuranyl)(5-methyl-3-phenyl-4-isoxazolyl)methanone (example 4) (100 mg, 0.31 mmol) was converted to the title compound [using 5-chloromethyl-1-methyl-1H-[1,2,4]triazole hydrochloride instead of N-(chloroacetyl)isopropylamine]which was obtained as a white solid (43 mg, 33%). MS m/e: 415.3 [M+H]$^+$.

EXAMPLE 15

[7-(3-Methyl-isoxazol-5-ylmethoxy)-benzofuran-2-yl]-(5-methyl-3-phenyl-isoxazol-4-yl)-methanone As described for example 6, (7-hydroxy-2-benzofuranyl)(5-methyl-3-phenyl-4-isoxazolyl)methanone (example 4) (100 mg, 0.31 mmol) was converted to the title compound (using 5-(chloromethyl)-3-methylisoxazole instead of ethanol) which was obtained as a white solid (99 mg, 76%). MS m/e: 415.1 [M+H]$^+$.

EXAMPLE 16

(6-Hydroxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 2,4-dihydroxybenzaldehyde instead of salicylaldehyde) which was obtained as a white solid (11 mg, 7%). MS m/e: 320.3 [M+H]$^+$.

EXAMPLE 17

(6-Methoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 2-hydroxy-4-methoxybenzaldehyde instead of salicylaldehyde) which was obtained as a white solid (95 mg, 57%). MS m/e: 334.1 [M+H]$^+$.

EXAMPLE 18

2-[2-(5-Methyl-3-phenyl-isoxazole-4-carbonyl)-benzofuran-6-yloxy]-1-(5-methyl-3-phenyl-isoxazol-4-yl)-ethanone As described for example 16, 4-(bromoacetyl)-5-methyl-3-phenylisoxazole (commercially available) (140 mg, 0.5 mmol) was converted to the title compound (using 2,4-dihydroxybenzaldehyde instead of salicylaldehyde) which was obtained as a white solid (46 mg, 18%). MS m/e: 519.3 [M+H]$^+$.

EXAMPLE 19

(5-Chloro-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 5-chlorosalicylaldehyde instead of salicylaldehyde) which was obtained as a white solid (114 mg, 68%). MS m/e: 338.1 [M+H]$^+$.

EXAMPLE 20

(5-Bromo-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 5-bromosalicylaldehyde instead of salicylaldehyde) which was obtained as a white solid (145 mg, 76%). MS m/e: 384.1/382.0 [M+H]$^+$.

EXAMPLE 21

(5-Methoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (using 2,5-dihydroxybenzaldehyde instead of salicylaldehyde) which was obtained as a white solid (63 mg, 40%). MS m/e: 320.3 [M+H]$^+$.

EXAMPLE 22

(5-Methoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound (2-hydroxy-5-methoxybenzaldehyde instead of salicylaldehyde) which was obtained as a white solid (73 mg, 44%). MS m/e: 334.1 [M+H]$^+$.

EXAMPLE 23

(5-Methyl-3-phenyl-isoxazol-4-yl)-(5-trifluoromethoxy-benzofuran-2-yl)-methanone As described for example 1, 4-(bromoacetyl)-5-methyl-3-phenylisoxazole (commercially available) (140 mg, 0.5 mmol) was converted to the title compound [using 5-(trifluoromethoxy)salicylaldehyde instead of salicylaldehyde] which was obtained as a white solid (159 mg, 82%). MS m/e: 388.4 [M+H]$^+$.

EXAMPLE 24

2-[2-(5-Methyl-3-phenyl-isoxazole-4-carbonyl)-benzofuran-5-yloxy]-1-(5-methyl-3-phenyl-isoxazol-4-yl)-ethanone As described for example 21, 4-(bromoacetyl)-5-methyl-3-phenylisoxazole (commercially available) (140 mg, 0.5 mmol) was converted to the title compound (using 2,5-dihydroxybenzaldehyde instead of salicylaldehyde) which was obtained as a white solid (27 mg, 10%). MS m/e: 519.3 [M+H]$^+$.

EXAMPLE 25

(4-Methoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound using (2-hydroxy-6-methoxybenzaldehyde instead of salicylaldehyde) which was obtained as a white solid (93 mg, 56%). MS m/e: 334.1 [M+H]$^+$.

EXAMPLE 26

(4,6-Dimethoxy-benzofuran-2-yl)-(5-methyl-3-phenyl-isoxazol-4-yl)-methanone

As described for example 1, 4-(bromoacetyl)-5-methyl-3-phenylisoxazole (commercially available) (140 mg, 0.5 mmol) was converted to the title compound using (4,6-dimethoxysalicylaldehyde instead of salicylaldehyde) which was obtained as a white solid (129 mg, 71%). MS m/e: 364.3 [M+H]$^+$.

EXAMPLE 27

(5-Methyl-3-phenyl-isoxazol-4-yl)-naphtho[2,1-b]furan-2-yl-methanone

As described for example 1, 4-(bromoacetyl)-5-methyl-3-phenylisoxazole (commercially available) (140 mg, 0.5 mmol) was converted to the title compound using (2-hydroxy-1-naphthaldehyde instead of salicylaldehyde) which was obtained as a white solid (136 mg, 77%). MS m/e: 354.1 [M+H]$^+$.

EXAMPLE 28

Benzofuran-2-yl-[3-(4-bromo-phenyl)-5-methyl-isoxazol-4-yl]-methanone (E)- and/or (Z)-4-Bromo-benzaldehyde-oxime To a suspension of 4-bromobenzaldehyde (20.0 g, 108 mmol) and hxdroxylamine hydrochloride (8.2 g, 119 mmol) in EtOH (8 mL) and water (24 mL) was added ice (46 g). Then a solution of NaOH (10.81 g, 270 mmol) in water (11 mL) was added dropwise within a 10 min period (temperature rises from −8° C. to +7° C.) whereupon most of the solid dissolves. After 30 min stirring at room temperature a white solid precipitated and the resulting mixture was then diluted with water and acidified with 4 N HCl. The white precipitate was then filtered off, washed with water and dried under high vacuum to afford the title compound (20.7 g, 96%). MS m/e: 198.0/200.1 $[M-H]^-$.

(E)- and/or (Z)-4-Bromo-N-hydroxy-benzenecarboximidoyl chloride

To a solution of (E)- and/or (Z)-4-bromo-benzaldehyde-oxime (7.15 g, 36 mmol) in DMF (36 mL) was added N-chlorosuccinimide (4.77 g, 45 mmol) portionwise over 1 h, keeping the temperature below 35° C. The reaction mixture was stirred under at room temperature overnight. The mixture was then poured onto ice-water, and extracted with ethyl acetate. The combined organic layers were then washed with water and brine, dried over $Na_2SO_4$ and evaporated to afford the title compound (7.6 g, 91%) as a light yellow solid after tritutation from heptane. MS m/e (EI): 233.0/234.9 $[M]^+$.

1-[3-(4-Bromo-phenyl)-5-methyl-isoxazol-4-yl]-ethanone

Acetylacetone (1.25 mL, 12 mmol) was added to a sodium ethoxide solution 3.09 N (3.95 mL, 12 mmol) in EtOH (22 mL) at room temperature. The resulting yellow solution was cooled with a ice-bath and a cloudy solution of (E)- and/or (Z)-4-bromo-N-hydroxy-benzenecarboximidoyl chloride (2.35 g, 10 mmol) in EtOH (8 mL) was added dropwise within 10 min keeping the temperature below 5° C. The light yellow suspension was stirred at room temperature for 3 h and then acidified with 6 N HCl and then evaporated. The resulting mixture was extracted with ethyl acetate and the combined organic layers were then washed with water and brine, dried over $Na_2SO_4$ and evaporated. Purification by chromatography ($SiO_2$, heptane:ethyl acetate:=100:0 to 7:3) afforded the title compound (2.35 g, 84%) as a light yellow oil. MS m/e: 280.1/282.1 $[M+H]^+$.

2-Bromo-1-[3-(4-bromo-phenyl)-5-methyl-isoxazol-4-yl]-ethanone

To a solution of 1-[3-(4-bromo-phenyl)-5-methyl-isoxazol-4-yl]-ethanone (2.49 g, 8.89 mmol) in carbontetrachloride (5.8 mL) and AcOH (0.3 mL) at 48° C. was added a solution of bromine (0.48 mL, 8.89 mmol) in carbontetrachloride (4.7 mL) over 10 min keeping the temperature below 50° C. After addition the reaction mixture was allowed to cool down to room temperature and poured into ice-water (20 mL). The layers were separated and the aqueous layer extracted with dichloromethane. The combined organic layers were then washed with water and brine, dried over $Na_2SO_4$ and evaporated. Purification by chromatography ($SiO_2$, heptane:ethyl acetate:=8:2) afforded the title compound (1.49 g, 47%) as a light yellow oil. MS m/e: 355.9/358.1/360.0 $[M+H]^+$.

Benzofuran-2-yl-[3-(4-bromo-phenyl)-5-methyl-isoxazol-4-yl]-methanone

As described for example 1, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (122 mg, 63%). MS m/e: 384.1/382.0 $[M+H]^+$.

EXAMPLE 29

[3-(4-Bromo-phenyl)-5-methyl-isoxazol-4-yl]-(7-fluoro-benzofuran-2-yl)-methanone As described for example 2, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (162 mg, 81%). MS m/e: 402.2/400.1 $[M+H]^+$.

EXAMPLE 30

[3-(4-Bromo-phenyl)-5-methyl-isoxazol-4-yl]-(7-hydroxy-benzofuran-2-yl)-methanone As described for example 4, 2-bromo-1-[3-(4-bromo-phenyl)-5-methyl-isoxazol-4-yl]-ethanone 180 mg, 0.5 mmol) [instead of 4-(bromoacetyl)-5-methyl-3-phenylisoxazole] was converted to the title compound which was obtained as a white solid (37 mg, 19%). MS m/e: 400.1/398.1 $[M+H]^+$.

EXAMPLE 31

[3-(4-Bromo-phenyl)-5-methyl-isoxazol-4-yl]-(7-methoxy-benzofuran-2-yl)-methanone As described for example 5, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (142 mg, 69%). MS m/e: 414.2/412.1 $[M+H]^+$.

EXAMPLE 32

[3-(4-Bromo-phenyl)-5-methyl-isoxazol-4-yl]-(7-ethoxy-benzofuran-2-yl)-methanone As described for example 28, 2-bromo-1-[3-(4-bromo-phenyl)-5-methyl-isoxazol-4-yl]-ethanone (180 mg, 0.5 mmol) was converted to the title compound using (3-ethoxysalicylaldehyde instead of salicylaldehyde) which was obtained as a white solid (126 mg, 59%). MS m/e: 428.2/426.0 $[M+H]^+$.

EXAMPLE 33

[3-(4-Bromo-phenyl)-5-methyl-isoxazol-4-yl]-(7-isopropoxy-benzofuran-2-yl)-methanone As described for example 6, 2-bromo-1-[3-(4-bromo-phenyl)-5-methyl-isoxazol-4-yl]-ethanone (120 mg, 0.30 mmol)) [instead of 4-(bromoacetyl)-5-methyl-3-phenylisoxazole] was converted to the title compound [using 2-propoanol instead of ethanol] which was obtained as a white solid (88 mg, 66%). MS m/e: 440.2/442.2 [M+H]$^+$.

EXAMPLE 34

[3-(4-Bromo-phenyl)-5-methyl-isoxazol-4-yl]-[7-(pyridin-2-ylmethoxy)-benzofuran-2-yl]-methanone As described for example 8, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (114 mg, 78%). MS m/e: 491.2/489.2 [M+H]$^+$.

EXAMPLE 35

[3-(4-Bromo-phenyl)-5-methyl-isoxazol-4-yl]-[7-(pyridin-3-ylmethoxy)-benzofuran-2-yl]-methanone As described for example 9, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (93 mg, 63%). MS m/e: 491.2/489.2 [M+H]$^+$.

EXAMPLE 36

[3-(4-Bromo-phenyl)-5-methyl-isoxazol-4-yl]-[7-(pyridin-4-ylmethoxy)-benzofuran-2-yl]-methanone As described for example 10, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (81 mg, 55%). MS m/e: 491.2/489.2 [M+H]$^+$.

EXAMPLE 37

2-{2-[3-(4-Bromo-phenyl)-5-methyl-isoxazole-4-carbonyl]-benzofuran-7-yloxy}-N-isopropyl-acetamide As described for example 13, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (82 mg, 55%). MS m/e: 499.2/497.3 [M+H]$^+$.

EXAMPLE 38

[3-(4-Bromo-phenyl)-5-methyl-isoxazol-4-yl]-[7-(2-methyl-2H-[1,2,4]triazol-3-ylmethoxy)-benzofuran-2-yl]-methanone As described for example 14, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (82 mg, 55%). MS m/e: 495.3/493.2 [M+H]$^+$.

EXAMPLE 39

[3-(4-Bromo-phenyl)-5-methyl-isoxazol-4-yl]-[7-(3-methyl-isoxazol-5-ylmethoxy)-benzofuran-2-yl]-methanone As described for example 15, 2-bromo-1-[3-(4-bromo-phenyl)-5-methyl-isoxazol-4-yl]-ethanone (120 mg, 0.3 mmol) [instead of 4-(bromoacetyl)-5-methyl-3-phenylisoxazole] was converted to the title compound which was obtained as a white solid (90 mg, 61%). MS m/e: 495.3/493.2 [M+H]$^+$.

EXAMPLE 40

[3-(4-Bromo-phenyl)-5-methyl-isoxazol-4-yl]-(6-hydroxy-benzofuran-2-yl)-methanone As described for example 16, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (8 mg, 4%). MS m/e: 400.0/398.1 [M+H]$^+$.

EXAMPLE 41

[3-(4-Bromo-phenyl)-5-methyl-isoxazol-4-yl]-(6-methoxy-benzofuran-2-yl)-methanone As described for example 17, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (144 mg, 70%). MS m/e: 414.2/412.1 [M+H]$^+$.

EXAMPLE 42

[3-(4-Bromo-phenyl)-5-methyl-isoxazol-4-yl]-(5-hydroxy-benzofuran-2-yl)-methanone As described for example 21, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (101 mg, 51%). MS m/e: 400.3/398.0 [M+H]$^+$.

EXAMPLE 43

[3-(4-Bromo-phenyl)-5-methyl-isoxazol-4-yl]-(5-methoxy-benzofuran-2-yl)-methanone As described for example 22, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (159 mg, 77%). MS m/e: 414.2/412.1 [M+H]$^+$.

EXAMPLE 44

[3-(4-Bromo-phenyl)-5-methyl-isoxazol-4-yl]-(4-methoxy-benzofuran-2-yl)-methanone As described for example 25, 2-bromo-1-[3-(4-bromo-phenyl)-5-methyl-isoxazol-4-yl]-ethanone (180 mg, 0.5 mmol) [instead of 4-(bromoacetyl)-5-methyl-3-phenylisoxazole] was converted to the title compound which was obtained as a white solid (109 mg, 53%). MS m/e: 414.2/412.1 [M+H]$^+$.

The invention claimed is:

1. A 3-aryl-isoxazole-4-carbonyl-benzofuran derivative of formula I

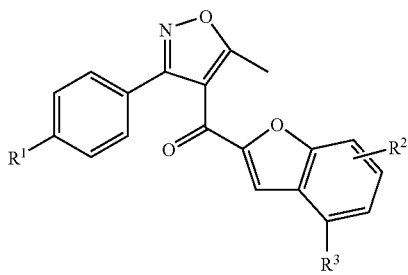

I wherein
$R^1$ is hydrogen or halogen;
$R^2$ is hydrogen, halogen, hydroxy, lower alkoxy, $OCF_3$, or —$OCH_2$—R,
$R^3$ is hydrogen or lower alkoxy; or
$R^2$ and $R^3$ together are —CH=CH—CH=CH—;
R is aryl or heteroaryl, each of which is optionally substituted by halogen or lower alkyl, or is C(O)NH-lower alkyl, or is —C(O)-heteroaryl, wherein the heteroaryl group is optionally substituted by lower alkyl or phenyl, or a pharmaceutically acceptable acid addition salt thereof.

2. A compound of claim 1, wherein $R^1$ is hydrogen.

3. A compound of claim 2, wherein $R^3$ is hydrogen.

4. A compound of claim 3, wherein $R^2$ is halogen, hydroxy, $OCF_3$ or lower alkoxy.

5. A compound of claim 4, wherein the compound is selected from the group consisting of
(7-bromo-benzofuran-2-yl)-(5-methyl-3-phenyl-isoxazol-4-yl)-methanone,
(7-hydroxy-2-benzofuranyl)(5-methyl-3-phenyl-4-isoxazolyl)methanone,
(7-methoxy-benzofuran-2-yl)-(5-methyl-3-phenyl-isoxazol-4-yl)-methanone,
(7-ethoxy-benzofuran-2-yl)-(5-methyl-3-phenyl-isoxazol-4-yl)-methanone,
(6-hydroxy-benzofuran-2-yl)-(5-methyl-3-phenyl-isoxazol-4-yl)-methanone,
(6-methoxy-benzofuran-2-yl)-(5-methyl-3-phenyl-isoxazol-4-yl)-methanone,
(5-methoxy-benzofuran-2-yl)-(5-methyl-3-phenyl-isoxazol-4-yl)-methanone,
(5-methoxy-benzofuran-2-yl)-(5-methyl-3-phenyl-isoxazol-4-yl)-methanone and
(5-methyl-3-phenyl-isoxazol-4-yl)-(5-trifluoromethoxy-benzofuran-2-yl)-methanone.

6. A compound of claim 3, wherein $R^3$ is hydrogen and $R^2$ is —$OCH_2$—C(O)NH-lower alkyl or —$OCH_2$-heteroaryl, wherein the heteroaryl group is optionally substituted by halogen or lower alkyl.

7. A compound of claim 6, wherein the compound is selected from the group consisting of
N-isopropyl-2-[2-(5-methyl-3-phenyl-isoxazole-4-carbonyl)-benzofuran-7-yloxy]-acetamide,
(5-methyl-3-phenyl-isoxazol-4-yl)-[7-(pyridin-2-ylmethoxy)-benzofuran-2-yl]-methanone,
(5-methyl-3-phenyl-isoxazol-4-yl)-[7-(pyridin-3-ylmethoxy)-benzofuran-2-yl]-methanone,
(5-methyl-3-phenyl-isoxazol-4-yl)-[7-(pyridin-4-ylmethoxy)-benzofuran-2-yl]-methanone and
[7-(3-methyl-isoxazol-5-ylmethoxy)-benzofuran-2-yl]-(5-methyl-3-phenyl-isoxazol-4-yl)-methanone.

8. A compound of claim 2, wherein $R^3$ is lower alkoxy and $R^2$ is lower alkoxy.

9. A compound of claim 8, wherein the compound is (4,6-dimethoxy-benzofuran-2-yl)-(5-methyl-3-phenyl-isoxazol-4-yl)-methanone.

10. A compound of claim 1, wherein $R^1$ is halogen.

11. A compound of claim 1, wherein $R^3$ is hydrogen and $R^2$ is hydrogen, hydroxy, lower alkoxy or —$OCH_2$C(O)NH-lower alkyl.

12. A compound of claim 11, wherein the compounds are selected from the group consisting of
benzofuran-2-yl-[3-(4-bromo-phenyl)-5-methyl-isoxazol-4-yl]-methanone,
[3-(4-bromo-phenyl)-5-methyl-isoxazol-4-yl]-(7-methoxy-benzofuran-2-yl)-methanone,
[3-(4-bromo-phenyl)-5-methyl-isoxazol-4-yl]-(7-ethoxy-benzofuran-2-yl)-methanone,
2-{2-[3-(4-bromo-phenyl)-5-methyl-isoxazole-4-carbonyl]-benzofuran-7-yloxy}-N-isopropyl-acetamide,
[3-(4-bromo-phenyl)-5-methyl-isoxazol-4-yl]-(6-hydroxy-benzofuran-2-yl)-methanone,
[3-(4-bromo-phenyl)-5-methyl-isoxazol-4-yl]-(6-methoxy-benzofuran-2-yl)-methanone,
[3-(4-bromo-phenyl)-5-methyl-isoxazol-4-yl]-(5-hydroxy-benzofuran-2-yl)-methanone and
[3-(4-bromo-phenyl)-5-methyl-isoxazol-4-yl]-(5-methoxy-benzofuran-2-yl)-methanone.

13. A compound of claim 10, wherein $R^3$ is lower alkoxy and $R^2$ is hydrogen.

14. A compound of claim 13, wherein the compound is [3-(4-bromo-phenyl)-5-methyl-isoxazol-4-yl]-(4-methoxy-benzofuran-2-yl)-methanone.

15. A compound of claim 1, wherein $R^3$ is hydrogen.

16. A compound of claim 1, wherein $R^3$ is lower alkoxy.

17. A compound of claim 1, wherein $R^2$ is —$OCH_2$R.

18. A compound of claim 17, wherein R is aryl.

19. A compound of claim 18, wherein R is phenyl, unsubstituted or substituted by halogen or lower alkyl.

20. A compound of claim 17, wherein R is heteroaryl.

21. A compound of claim 20, wherein R is pyridinyl.

22. A compound of claim 20, wherein R is oxazolyl.

23. A compound of claim 20, wherein R is triazolyl.

24. A compound of claim 17, wherein R is C(O)NH-lower alkyl.

25. A compound of claim 1, wherein $R^2$ is hydrogen, halogen, hydroxyl, $OCH_3$, or $OCF_3$.

26. A compound of claim 1, wherein $R^2$ and $R^3$ together are —CH=CH—CH=CH—.

27. A pharmaceutical composition comprising a therapeutically effective amount of a compound of formula I

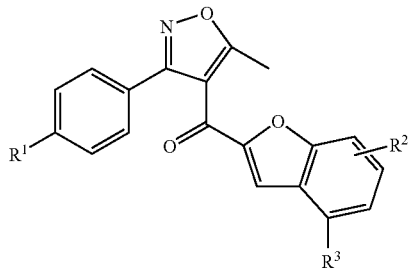

wherein
$R^1$ is hydrogen or halogen;
$R^2$ is hydrogen, halogen, hydroxy, lower alkoxy, $OCF_3$, or —$OCH_2$—R,
$R^3$ is hydrogen or lower alkoxy; or
$R^2$ and $R^3$ together are —CH=CH—CH=CH—;
R is aryl or heteroaryl, each of which is optionally substituted by halogen or lower alkyl, or is C(O)NH-lower alkyl, or is —C(O)-heteroaryl, wherein the heteroaryl group is optionally substituted by lower alkyl or phenyl,
or a pharmaceutically acceptable acid addition salt thereof and a pharmaceutically acceptable carrier.

* * * * *

UNITED STATES PATENT AND TRADEMARK OFFICE
CERTIFICATE OF CORRECTION

PATENT NO. : 7,388,025 B2  Page 1 of 1
APPLICATION NO. : 11/590571
DATED : June 17, 2008
INVENTOR(S) : Buettelmann et al.

It is certified that error appears in the above-identified patent and that said Letters Patent is hereby corrected as shown below:

IN THE CLAIMS:

• Claim 1, Column 19, line 35: "-CH=CH-CH=-CH-;" should read
-- -CH=CH-CH=CH- --.

Signed and Sealed this

Twenty-sixth Day of January, 2010

David J. Kappos
*Director of the United States Patent and Trademark Office*